(12) United States Patent
Daniel et al.

(10) Patent No.: US 12,420,002 B2
(45) Date of Patent: Sep. 23, 2025

(54) DIALYSIS MACHINE AND CLEANING METHOD FOR THE DIALYSIS MACHINE

(71) Applicant: FRESENIUS MEDICAL CARE DEUTSCHLAND GMBH, Bad Homburg (DE)

(72) Inventors: Pia Daniel, Bodman (DE); Stephan Goessmann, Friedrichsdorf (DE); Klaus Karl, Alzenau (DE); Georg Verch, Wiesbaden (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 223 days.

(21) Appl. No.: 18/318,050

(22) Filed: May 16, 2023

(65) Prior Publication Data

US 2023/0302208 A1 Sep. 28, 2023

Related U.S. Application Data

(62) Division of application No. 16/462,393, filed as application No. PCT/EP2017/079566 on Nov. 17, 2017, now Pat. No. 11,684,706.

(30) Foreign Application Priority Data

Nov. 19, 2016 (DE) ...................... 10 2016 013 875.0

(51) Int. Cl.
*A61M 1/16* (2006.01)
(52) U.S. Cl.
CPC .......... *A61M 1/1656* (2013.01); *A61M 1/169* (2013.01); *A61M 1/1688* (2014.02)

(58) Field of Classification Search
CPC .. A61M 1/1656; A61M 1/169; A61M 1/1688; A61M 1/168; A61M 1/1666; A61M 1/3462; A61M 1/3643; A61M 1/3649
See application file for complete search history.

(56) References Cited

U.S. PATENT DOCUMENTS

| 5,972,223 | A | 10/1999 | Jonsson |
| 2004/0082903 | A1 | 4/2004 | Micheli |
| 2008/0230450 | A1 | 9/2008 | Burbank |
| 2010/0116740 | A1* | 5/2010 | Fulkerson ........... A61M 1/1696 210/87 |
| 2012/0175296 | A1 | 7/2012 | Wehmeyer |

FOREIGN PATENT DOCUMENTS

| CN | 103153442 | 6/2013 |
| CN | 103313739 | 9/2013 |
| CN | 1038133816 | 5/2014 |
| CN | 103845768 | 6/2014 |

(Continued)

OTHER PUBLICATIONS

English language machine translation of WO2013183599, 14 pages, No Date.*

*Primary Examiner* — Pranav N Patel
(74) *Attorney, Agent, or Firm* — Kilyk & Bowersox, P.L.L.C.

(57) ABSTRACT

The invention relates to a dialysis treatment unit in which the connecting line to the central concentrate supply is also rinsed in the rinsing or cleaning process in order to prevent deposits therein.

16 Claims, 2 Drawing Sheets

(56) References Cited

FOREIGN PATENT DOCUMENTS

| | | | |
|---|---|---|---|
| CN | 105233356 | 1/2016 | |
| DE | 10256584 | 5/2004 | |
| DE | 102011008223 | 7/2012 | |
| EP | 0622086 | 11/1994 | |
| JP | 2010253130 | 11/2010 | |
| WO | 2007148442 | 12/2007 | |
| WO | 2012166377 | 12/2012 | |
| WO | WO-2013183599 A1 * | 12/2013 | ............ A61M 1/165 |

* cited by examiner

DIALYSIS MACHINE AND CLEANING METHOD FOR THE DIALYSIS MACHINE

TECHNICAL FIELD

The invention relates to a dialysis machine, which requires less maintenance and also relates to a cleaning method for reducing the need for maintenance.

BACKGROUND

In chronic hemodialysis for treatment of renal insufficiency, approximately 120-180 liters of dialysis solution are needed per treatment.

This dialysis solution is usually prepared by the treatment machine on site by diluting and mixing an acidic concentrate and a basic concentrate with dialysis water (permeate).

The basic concentrate consists of pure bicarbonate and is prepared almost exclusively as a dry concentrate.

The acidic concentrate is usually supplied as a mixture of table salt (approximately 75% by weight), an acid, KCl, $CaCl_2$, $MgCl_2$ and glucose. This concentrate is usually supplied as a liquid concentrate in containers such as canisters or bags, which supply an adequate amount of concentrate for one or two treatments, i.e., 5-10 liters of concentrate. These canisters are brought directly to the treatment machine by the nursing personnel. The treatment machine then has a concentrate suction wand, for example, with which the concentrate is removed from the canister.

Dialysis clinics, in which several patients are treated at the same time, often have a central concentrate supply. These central concentrate supplies yield the liquid concentrate from a larger packaging unit, for example (e.g., 300-400 liters) through one or more ring lines to the individual treatment sites where, the treatment machines are then connected to this ring line by means of connecting tubing. Each treatment machine can be connected simultaneously to two different concentrate ring lines by means of separate connections.

These central concentrate supply lines offer the advantage that, first, the heavy canisters need not be brought to the treatment site and, second, the volume of waste is reduced due to the larger containers.

It is advantageous to use individual canisters because that makes it possible to adjust the composition of the dialysis solution to the individual requirements of each individual patient being treated. Thus, different concentrations of electrolytes, different acids or even different concentrations of glucose may be indicated, depending on the patient.

In contrast with that, only a uniform concentrate, which is not necessarily optimized for all patients, can be made available per existing ring line. The number of available ring lines is usually limited to one or two.

If concentrate canisters are frequently used to prepare the dialysis solution and/or multiple concentrate ring lines are connected to the dialysis machine, then the contents of the unused concentrate connecting tubing, which are then unused, are left standing, potentially for a longer period of time, which can lead to the following problem.

The connecting tubing from the treatment machine to the ring line of the central concentrate supply is made of plastic. Water can diffuse through this plastic tubing to a slight extent, so there is an increase in the concentration of the concentrate present in the tubing, in particular when there is a prolonged pause in use. Since the liquid concentrates are salt solutions approaching saturation, there may therefore be a buildup of salt crystals in the tubing. These salt crystals are then rinsed into the machine during the next use of the central concentrate supply and can lead to problems there, which can necessitate an unscheduled service call on the machine.

The object of the present invention consists of supplying a treatment machine for hemodialysis, in which the formation of crystals in the treatment tubing of the treatment machine for the central concentrate supply is prevented.

SUMMARY OF THE INVENTION

According to the teaching of the present invention, this object is achieved by a device as well as a method, as described herein.

In accordance with the present teaching, a dialysis treatment unit having a preparation unit for dialysis solution is disclosed. This preparation unit serves to prepare a ready-to-use dialysis solution from at least one concentrate and one dialysis water (permeate). The concentrate can be supplied through a central concentrate supply. This central concentrate supply prepares liquid concentrate through a line means, for example, a ring line, to several treatment stations having dialysis treatment units. The dialysis treatment unit has a connecting means, which can be connected to the line means of the central concentrate supply. This connecting means is connected to a concentrate line of the preparation unit. At least one valve is provided in this concentrate line, by means of which the transfer of concentrate from the connecting means to the concentrate line of the preparation unit can be controlled by a control unit. This control unit is configured to cause the liquid concentrate to be transferred from the connecting means to the concentrate line during a rinsing process and/or a cleaning operation.

In the connecting means, the concentrate which flows out of the line means of the connecting means and into the dialysis machine is replaced by fresh concentrate from the line means of the central concentrate supply. Since these rinsing and/or cleaning methods are carried out regularly, the liquid concentrate in the connecting means is replaced regularly, independently of the concentrate source used. The increase in concentration of the concentrate and the formation of crystals in the connecting means are therefore prevented.

The transfer of concentrate from the connecting means into the concentrate line can be created by opening the at least one valve in the concentrate line, if there is a higher pressure in the connecting means than in the concentrate line between the at least one valve and the preparation unit. The line means of the central concentrate supply is under an excess pressure as a standard. This excess pressure may amount to 0.05 bar to 2 bar, for example. A reduced pressure of −0.1 bar or less, for example, may exist in the concentrate line between the at least one valve and the preparation unit.

Several valves may also be provided in series connection in the concentrate line, and then may be opened at the same time. When the valves are opened, the pressure is equalized by transferring the concentrate out of the connecting means and into the concentrate line. On opening the valves, the pressure is equalized by transferring the concentrate out of the connecting means and into the concentrate line.

The opening of the valve or valves may take place over a period of 0.5 to 5 s, so that a sufficient amount of concentrate, e.g., 12 mL, is transferred.

The amount of concentrate transferred depends on the length of the connecting means, the difference in pressure, the viscosity of the concentrate and the flexibility of the central concentrate supply, for example. At a pressure of −0.2 bar in the concentrate line of the dialysis machine and with a connecting means 3 meters long, approximately 12 milliliters of concentrate per second are drawn in the valve opening may thus amount to 1 s, for example.

The valve opening and thus the transfer of the concentrate may preferably take place in an early phase of the rinsing or cleaning method, e.g., the rinsing or cleaning solutions are conveyed into the concentrate line. This ensures that crystals, which enter the concentrate line together with the concentrate, for example, are reliably rinsed out. Furthermore, chemical reactions between the disinfection solution and the concentrate are prevented for the case when dialysis water (permeate), cleaning solutions or disinfection solutions are conveyed into the concentrate line after rinsing solutions, e.g., dialysis water (permeate).

The connecting means may be formed by plastic tubing, e.g., a PVC tubing.

The rinsing or cleaning method may be a disinfection method.

In addition, the invention also relates to a rinsing process for a dialysis treatment unit. This rinsing process serves as a preparation method for the dialysis treatment unit, which is carried out regularly between two days of treatment in order to provide a clean, disinfected dialysis treatment unit for the next treatment. In addition to the rinsing steps with dialysis water (permeate) or cleaning solutions or disinfection solutions, the rinsing process also includes a rinsing step for the connecting means to the central concentrate supply. In the rinsing process for the dialysis treatment unit, comprising a preparation unit for dialysis solution having a concentrate line with at least one valve and having at least one connecting means for connecting the concentrate line to a line means of a central concentrate supply unit, concentrate is first transferred out of the connecting means and into the concentrate line to prevent formation of crystals, and then the rinsing steps are formed are carried out to clean an d disinfect the dialysis treatment unit.

The concentrate can be transferred out of the connecting means and into the concentrate line by supplying a valve in the concentrate line, adjusting a reduced pressure in the concentrate line between this valve and the preparation unit and opening this valve for a predetermined period of time. Following the equalization of pressure, then a certain volume segment of liquid concentrate is transferred out of the connecting means and into the concentrate line. After closing the valve, the liquid concentrate that has flowed out of the connecting means is replaced by fresh concentrate from the central concentrate supply unit, which has the correct composition. The increase in concentration of the concentrate in the connecting means to the central concentrate supply is prevented. The reduced pressure set in the concentrate line may amount to −0.1 bar or less. The valve opening may take place for 0.5 to 5 s. The rinsing process may be a method for disinfection of the dialysis treatment unit.

DETAILED DESCRIPTION OF ONE EXEMPLARY EMBODIMENT

Figure 1:
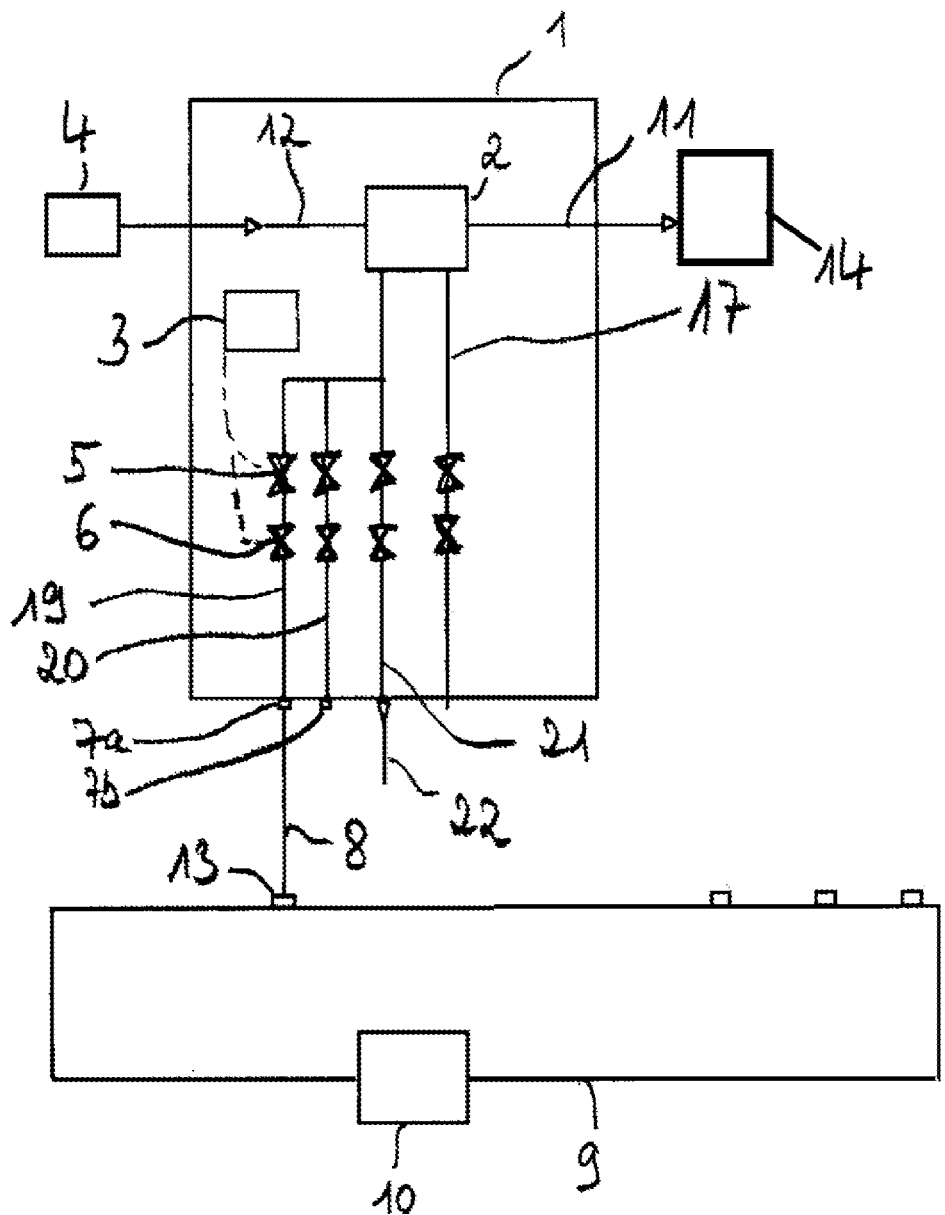
FIG. 1 shows schematically the design of a dialysis treatment unit.
Figure 2:
FIG. 2 shows schematically the flow chart of the method.

The Dialysis treatment unit 1 prepares dialysis solution online from dialysis water (permeate) and concentrate by means of a preparation unit 2. The dialysis water (permeate) is supplied to the preparation unit 2 from a reverse osmosis system 4 through the line 12. The dialysis solution is usually prepared by diluting and mixing an acidic concentrate and a basic concentrate with dialysis water (permeate). A concentrate line 17 is provided for the basic concentrate. However, it is also possible that a connection to a central concentrate supply unit (not shown) for the basic concentrate is provided. The ready-to-use dialysis solution is then supplied to a treatment module 14, from which the dialysis solution is then transferred further to a dialysis filter (not shown), for example, through the line 11.

In modern dialysis treatment units, several options can be selected for the acidic concentrate in most cases. For example, the acidic concentrate can be removed from the canister with a concentrate suction wand 22 and transported to the preparation unit 2 through a concentrate line 21. However, the acidic concentrate can also be supplied from a central concentrate supply 10. The dialysis treatment unit 1 has connectors 7a and 7b for the connection to a central concentrate supply 10. One end of a connecting means 8, for example, a plastic tubing, may be connected to the connector 7a. The second end of the connecting means 8 is connected to a connector 13 of the ring line 9 of the central concentrate supply 10. Whereas a fluid exchange is always taking place in the ring line 9, the passage in the connecting means 8 exists only when concentrate is being obtained only from the central concentrate supply 10. The dialysis treatment unit 1 has a control unit 3, which is configured to open the valves 5 and 6 during a cleaning method. Since an excess pressure of 0.5 to 2.0 bar prevails as the standard in the ring line 9 of a central concentrate supply unit 10 and a reduced pressure of −0.2 bar prevails behind the valves 5 and 6 in the concentrate line 19, a certain fluid volume is conveyed into the concentrate line 19 with the opening of the valves 5 and 6. Thus, with a valve opening for one second, approximately 12 mL concentrate is conveyed. Since the cleaning method is used regularly, i.e., whenever the dialysis treatment unit 1 is used, there is a regular exchange of concentrate in the connecting means 8. This prevents the formation of deposits in the connecting means 8. Additional solutions used in the rinsing process, such as disinfectants, can also be sent to the preparation unit 2 and distributed from there (not shown). Another concentrate line 20 is also shown.

In contrast with the known rinsing processes, the rinsing process has an additional process step, namely the transfer of a volume segment of liquid concentrate out of the connecting means 8 and into the concentrate line 19. The connecting means 8 is then supplied with fresh liquid concentrate through the ring line 9 of the central concentrate supply. Then in the dialysis treatment unit, the liquid-carrying lines of the dialysis treatment unit are rinsed with dialysis water (permeate) to rinse it clear of the concentrate. Following that, the lines are then rinsed with cleaning solution or disinfectant solution and the other steps are carried out to clean the machine. The intermediate rinsing step prevents chemical reactions of the liquid concentrate with cleaning solution or disinfectant solution, for example.

The invention claimed is:

1. A method for rinsing a dialysis treatment unit, the dialysis treatment unit comprising a preparation unit for preparing a dialysis solution, a control unit, and a central concentrate supply unit that comprises a supply line, wherein the preparation unit for preparing the dialysis solution comprises a liquid concentrate line, a valve in the liquid concentrate line, and at least one connector line connecting the liquid concentrate line to the supply line of the central concentrate supply unit, and wherein the method comprises:
- rinsing the at least one connector line by controlling, with the control unit, the valve in the liquid concentrate line, so as to (i) form a pressure in the liquid concentrate line that is a reduced pressure relative to a pressure in the supply line, and (ii) open the valve to cause liquid concentrate to be transferred out of the at least one connector line and into the liquid concentrate line thereby preventing formation of crystals in the at least one connector line; and then
- rinsing the liquid concentrate line with a rinsing or cleaning solution after the rinsing of the at least one connector line.

2. The rinsing process method according to claim 1, further comprising rinsing with dialysis water or permeate before rinsing with the rinsing or cleaning solution.

3. The method according to claim 1, wherein the control unit controls the transfer of concentrate from the at least line connector into the liquid concentrate line by causing a negative pressure to be established in the liquid concentrate line between the valve and the preparation unit, and by operating the valve in the liquid concentrate line.

4. The method according to claim 3, wherein the negative pressure is a pressure of −0.1 bar or less.

5. The method according to claim 3, wherein the valve is opened for 0.5 to 5 s.

6. The method according to claim 1, further comprising disinfecting the dialysis treatment unit.

7. The method according to claim 1, further comprising rinsing to clean or to clean and disinfect the dialysis treatment unit.

8. The method according to claim 1, further comprising, after the rinsing of the liquid concentrate line with a rinsing or cleaning solution, drawing fresh liquid concentrate for preparing a dialysis solution through the supply line and into the at least one connector line.

9. The method according to claim 8, wherein the fresh liquid concentrate for preparing a dialysis solution is drawn into the at least one connector line before the rinsing of the liquid concentrate line.

10. The method according to claim 8, further comprising drawing the fresh liquid concentrate for preparing a dialysis solution, into the liquid concentrate line.

11. The method according to claim 1, wherein the preparation unit further comprises a series of valves, the valve is part of the series of valves, and the controlling, with the control unit, comprises controlling the series of valves to open the series of valves.

12. The method according to claim 1, wherein the preparation unit further comprises a second concentrate line, a second valve in the second concentrate line, and a second connector line that connects the second concentrate line to the second supply line, and wherein the method further comprises:
- connecting the second supply line to a supply of second concentrate; and
- drawing the second concentrate through the second supply line, through the second connector line, through the second valve, and into the second concentrate line.

13. The method according to claim 12, wherein the preparation unit comprises a second series of valves in the second concentrate line, the second valve is part of the second series of valves, and the drawing of the second concentrate comprises drawing the second concentrate through the second series of valves.

14. The method according to claim 1, further comprising:
- connecting different dialysis machines to the supply line of the central concentrate supply unit; and
- respectively drawing the liquid concentrate for preparing a dialysis solution, into each of the different dialysis machines.

15. The method according to claim 14, further comprising:
- connecting the different dialysis machines to a second supply line of a second central concentrate supply unit; and
- respectively drawing a second concentrate through the second supply line, into each of the different dialysis machines, wherein the second concentrate differs from the liquid concentrate for preparing a dialysis solution.

16. The method according to claim 1, wherein the method further comprises, prior to the rinsing of the at least one connector line:
- connecting the supply line to a supply of concentrate for preparing a dialysis solution; and
- drawing concentrate from the supply of concentrate for preparing a dialysis solution, from the supply line, through the at least one connector line, and into the liquid concentrate line.

* * * * *